(12) United States Patent
Kaushansky

(10) Patent No.: US 9,138,519 B2
(45) Date of Patent: Sep. 22, 2015

(54) MULTI POWER SOURCE POWER SUPPLY

(75) Inventor: Yefim Kaushansky, North Haledon, NJ (US)

(73) Assignee: MAQUET Cardiovascular LLC, Mahwah, NJ (US)

( * ) Notice: Subject to any disclaimer, the term of this patent is extended or adjusted under 35 U.S.C. 154(b) by 1131 days.

(21) Appl. No.: 13/089,128

(22) Filed: Apr. 18, 2011

(65) Prior Publication Data

US 2012/0265004 A1    Oct. 18, 2012

(51) Int. Cl.
| | |
|---|---|
| A61N 1/00 | (2006.01) |
| A61M 1/12 | (2006.01) |
| A61M 1/10 | (2006.01) |
| H02J 9/06 | (2006.01) |
| H01M 2/10 | (2006.01) |

(52) U.S. Cl.
CPC ............. *A61M 1/127* (2013.01); *A61M 1/1072* (2013.01); *H02J 9/061* (2013.01); *A61M 2205/8206* (2013.01); *H01M 2/1022* (2013.01)

(58) Field of Classification Search
CPC . A61M 1/127; A61M 1/1072; A61M 1/8206; H02J 9/061; H01M 2/1022
USPC .......................................................... 600/18
See application file for complete search history.

(56) References Cited

U.S. PATENT DOCUMENTS

| | | | |
|---|---|---|---|
| 5,011,468 A | 4/1991 | Lundquist et al. | |
| 5,328,781 A | 7/1994 | Mikake | |
| 5,508,569 A | 4/1996 | Nishino | |
| 5,824,431 A | 10/1998 | Tsurumaru et al. | |
| 6,287,140 B1 | 9/2001 | Itoh | |
| 6,293,463 B1 | 9/2001 | Kato et al. | |
| 6,306,538 B1 | 10/2001 | Saitoh et al. | |
| 6,730,432 B1 | 5/2004 | Grosfeld et al. | |
| 6,763,594 B2 | 7/2004 | Foreman | |
| 2003/0055309 A1* | 3/2003 | Kaushansky et al. | 600/18 |
| 2008/0028237 A1 | 1/2008 | Knight | |
| 2010/0225170 A1 | 9/2010 | Hjort et al. | |
| 2010/0264738 A1* | 10/2010 | Murtha et al. | 307/66 |

FOREIGN PATENT DOCUMENTS

| | | |
|---|---|---|
| EP | 0825520 A1 | 2/1998 |
| EP | 1030240 A2 | 8/2000 |
| GB | 2311408 A | 9/1997 |

OTHER PUBLICATIONS

Product Brochure—CS300 IABP—Product Features—2009 Publication—Maquet Cardiovascular LLC. U.S.A.

(Continued)

*Primary Examiner* — Christopher D Koharski
*Assistant Examiner* — Roland Dinga

(57) ABSTRACT

A multiple power-source housing adapted to prevent simultaneous removal of more than a single power source, such as a battery, at a time. In an example embodiment, the power-source housing is used to house batteries for an intra-aortic balloon pump, which use battery power during transport. The power-source housing holds a first and second power source. When the first power source is removed, a mechanism, such as a knob, prevents simultaneous removal of the second power source or removal of the second power source until the first power source is replaced. Similarly, when the second power source is removed the mechanism prevents simultaneous removal of the first power source or removal of the first power source until the second power source is replaced.

23 Claims, 11 Drawing Sheets

(56) References Cited

OTHER PUBLICATIONS

Product Brochure—CS100 IABP—Intelligent Counterpulsation—2010 Publication—Maquet Cardiovascular LLC. U.S.A.
Operators Guide—The CS100/CS100i Abbreviated Operator's Guide—2009 Publication—Maquet Cardiovascular LLC. U.S.A.
Operators Guide—Datascope Abbreviated Operator's Guide for the System 97 Intra-Aortic Balloon Pump—Published prior to 2009—Datascope Corp. U.S.A.
Brochure—Sensation and CS300 IABP System Smaller Meets Faster—Published in 2009—Maquet Cardiovascular LLC. U.S.A.
Brochure—CS300 IABP Product Features—Published in 2009—Maquet Cardiovascular LLC. U.S.A.
Brochure—CS100—Intelligent Counterpulsation—Published prior to 2009—Datascope Corp. U.S.A.
Brochure—Datascope System 97—Published Prior to 2009—Datascope Corp. U.S.A.
Abbreviated Operation and Troubleshooting Guide—Arrow AutoCat2 WAVE IAB Abreviated Operation and Troubleshooting Guide—2005—Arrow International, Inc.
Troubleshooting Brochure—Troubleshooting Beyond the Basics—Arrow Intra-Aortic Balloon Pump—1999—Arrow International, Inc.
Educational Material—AutoCAT2 Series Intra-Aortic Balloon Pump—Timing, Triggering, and Troubleshooting—2005—Arrow International, Inc. U.S.A.
Brochure—Changing Disposable Helium Tank—2005—Arrow International, Inc. U.S.A.
Educational Materials—ACAT1 Plus Intra-Aortic Balloon Pump—Timing, Triggering, and Troubleshooting—2005—Arrow International, Inc. U.S.A.
Brochure/Flyer—Feature Comparison—Arrow AutoCAT2 Series—2006—Arrow International, Inc. U.S.A.
International Search Report and Written Opinion from the International Search Authority for PCT/US2012/034116, Mailed Jun. 20, 2013, European Patent Office.
Service Manual, Datascope Passport 2 / Datascope Passport 2LT, Copyright 2008, Mindray DS USA, Inc., Dec. 2008.

* cited by examiner

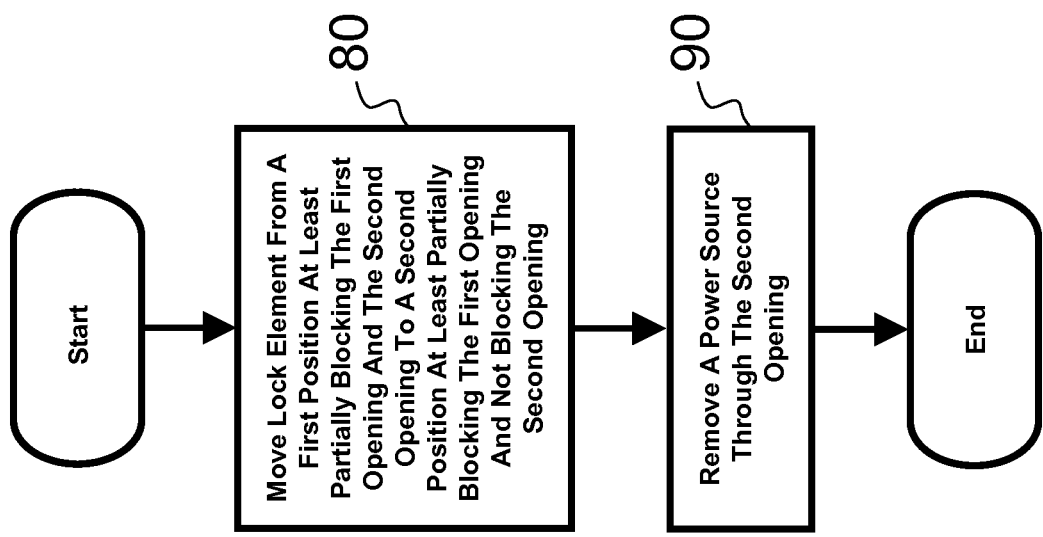

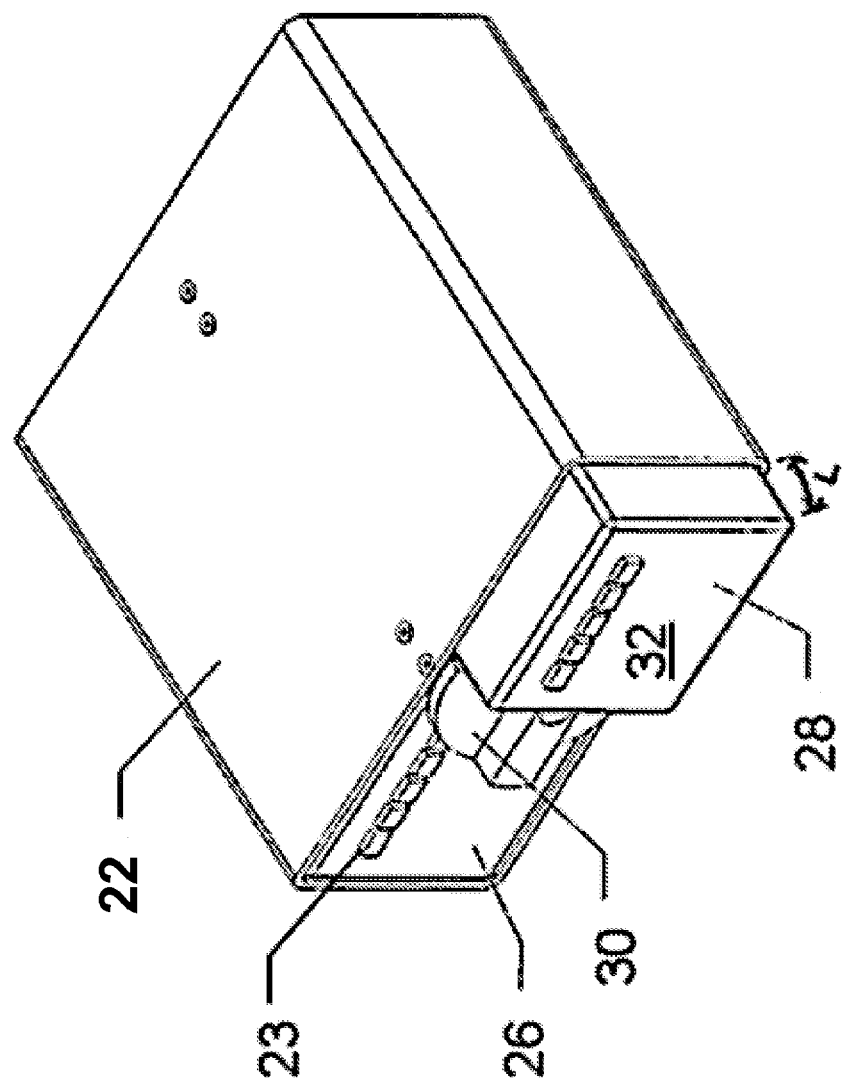

MULTI POWER SOURCE POWER SUPPLY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention generally relates to a battery housing. An exemplary embodiment of the present invention relates to a battery housing for a medical device such as an intra-aortic balloon pump.

2. Description of Related Art

Intra-aortic balloon pumps (IABPs) are used to provide pneumatic assistance to a failing or weakened heart. Often this therapy must be sustained as patients are transported within or between medical facilities.

When an IABP is in a stationary mode, it is typically powered by the medical facility's AC power. The IABP incorporates an internal back-up battery used to provide power during transport or in case of AC power loss. Typically, the battery is integrated into an internal battery compartment and is not readily accessible for replacement while the IABP is in operation. Therefore, if the battery is allowed to discharge, the IABP becomes unusable for patient transport and must be connected to an AC power source for recharging, some times for several hours.

IABPs typically use lead acid battery technology. This type of battery is heavy, bulky, and requires fasteners to connect to the terminals. Due to the heavy weight of a lead-acid battery, heavy brackets are required to secure it within the IABP. Further, lead-acid batteries have a finite number of charge/discharge cycles after which they are no longer capable of retaining a charge.

Replacement of a battery of this type is also labor intensive. Replacement typically requires a technician to disassemble a portion of the IABP so as to disconnect the battery compartment and remove it from the IABP. The battery compartment must then be partially disassembled before the battery can be removed. The technician then reverses this process to install the new battery. During this time, the IABP is out of service.

Battery technology has made significant advances over the past years. As a result, new batteries weigh less, take less physical space, and have higher power density ratings than their predecessors. A need exists for a medical unit such as an IABP with an improved, safer, and more easily replaceable battery.

SUMMARY OF THE INVENTION

A medical device, such as an intra-aortic balloon pump, according to an example embodiment of the present invention includes a pump, a lock element, a power-source housing, and a control unit adapted to control the pump. An interior of the power-source housing including a first housing part and a second housing part. The first housing part is configured to hold a first power source. The second housing part is configured to hold a second power source. The first housing part includes a first opening large enough for the first power source to pass through. The second housing part includes a second opening large enough for the second power source to pass through. The power-source housing is accessible such that the first power source and the second power source can be replaced without dismantling the intra-aortic balloon pump. The power-source housing is configured such that when the first power source is being removed from the first housing part the lock element prevents simultaneous removal of the second power source from the second housing part and when the second power source is being removed from the second housing part the lock element prevents simultaneous removal of the first power source from the first housing part.

According to an example embodiment, the first power source is capable of being replaced while the second power source is powering the intra-aortic balloon pump and the second power source is capable of being replaced while the first power source is powering the intra-aortic balloon pump.

According to an example embodiment, each of the first and second power sources are independently capable of providing sufficient power to run the intra-aortic balloon pump for a predetermined period of time.

According to an example embodiment, at least one of the first power source and the second power source is a battery.

According to an example embodiment, at least one of the first power source and the second power source is an AC power supply or a DC power supply.

According to an example embodiment, the first power source is a battery and the second power source is an AC power supply or a DC power supply. Further, the first power source and the second power source may have similar physical dimensions.

According to an example embodiment, the lock element includes a mechanism positioned between the first and second openings. The mechanism is movable between (i) a first position at least partially blocking the first opening but not the second opening, (ii) a second position at least partially blocking the first opening and the second opening, and (iii) a third position at least partially blocking the second opening but not the first opening.

According to an example embodiment, the lock element includes a solenoid configured to move a rod forward such that a forward end of the rod passes into a recess in the lock element to fix movement of the lock element.

According to an example embodiment, the power-source housing is configured to facilitate removal of the first power source. When the first housing part is transitioned from a locked state to an unlocked state, via the lock element, the first power source is shifted forward in the power-source housing a predetermined distance by one or more mechanisms in the power-source housing.

According to an example embodiment, the one or more mechanisms in the power-source housing are spring-based.

According to an example embodiment, the power-source housing is configured to facilitate removal of the second power source. When the second housing part is transitioned from a locked state to an unlocked state, via the lock element, the second power source is shifted forward in the power-source housing a predetermined distance by the one or more mechanisms in the power-source housing.

According to an example embodiment, the mechanism includes a first rod. The first rod is configured such that placing the first power source in the first housing part to a sufficient depth within the power-source housing shifts the first rod rearward away from the first opening against the force of a first spring-based element. Subsequent removal of the first battery causes the first rod to move forward such that a forward end of the first rod passes into a recess in the lock element while in the third position.

According to an example embodiment, the mechanism further includes a second rod. The second rod is configured such that placing the second power source in the second housing part to a sufficient depth within the housing shifts the second rod rearward away from the second opening against the force of a second spring-based element. Subsequent removal of the second battery causes the second rod to move forward such that a forward end of the second rod passes into a recess in the lock element while in the first position.

According to an example embodiment, the mechanism further includes a first solenoid and a second solenoid. The lock element contains a first partial recess groove, configured to engage a first rod controlled by the first solenoid, and a second partial recess groove, configured to engage a second rod controlled by the second solenoid. The first partial recess groove when engaged by the first rod both allows motion between the first position and the second position and restricts motion from the second position to the third position. The second partial groove when engaged by the second rod both allows motions between the second position and the third position and restricts motion from the second position to the first position.

A container according to an example embodiment of the present invention includes a housing and a lock element. The housing defines a first housing part and a second housing part. The first housing part is configured to hold a first power source. The second housing part is configured to hold a second power source. The first housing part includes a first opening large enough for the first power source to pass through. The second housing part includes a second opening large enough for the second power source to pass through. The container is configured such that when the first power source is being removed from the first housing part, the lock element prevents simultaneous removal of the second power source from the second housing part and when the second power source is being removed from the second housing part, the lock element prevents simultaneous removal of the first power source from the first housing part.

According to an example embodiment, the container is configured to facilitate removal of the first power source. When the first housing part is transitioned from a locked state to an unlocked state, via the lock element, the first power source is shifted forward in the housing a predetermined distance by one or more mechanisms in the housing.

According to an example embodiment, the container is configured to facilitate removal of the second power source. When the second housing part is transitioned from a locked state to an unlocked state, via the lock element, the second power source is shifted forward in the housing a predetermined distance by the one or more mechanisms in the housing.

According to an example embodiment, the lock element includes a mechanism positioned between the first and second housing parts. The mechanism includes a knob configured to be moved to (i) a first position at least partially blocking the first opening but not the second opening, (ii) a second position at least partially blocking the first opening and the second opening, and (iii) a third position at least partially blocking the second opening but not the first opening.

According to an example embodiment, movement of the knob from the first position to either the second or third position is achieved through rotation of the knob.

A device according to an example embodiment of the present invention includes a power source, a lock element, and a power-source housing. An interior of the power-source housing includes a first housing part and a second housing part. The first housing part is configured to hold a first power source. The second housing part is configured to hold a second power source. The first housing part includes a first opening large enough for the first power source to pass through. The second part includes a second opening large enough for the second power source to pass through. The power-source housing is configured such that when the first power source is being removed from the first housing part the lock element prevents simultaneous removal of the second power source from the second housing part and when the second power source is being removed from the second housing part the lock element prevents simultaneous removal of the first power source from the first housing part.

The present invention is not limited to medical equipment. In an example embodiment, the device is a piece of machinery, such as drill, or an electric car, or a computer, or a mobile phone, or any other device that would benefit from an uninterrupted power supply.

A method, according to an exemplary embodiment of the present invention, involves loading and replacing one more batteries in an intra-aortic balloon pump. The intra-aortic balloon pump including a housing containing at least a first and second battery. The method includes (i) inserting the first battery into a first battery compartment in the housing, (ii) inserting the second battery into a second battery compartment in the housing, (iii) positioning a knob, rotatably connected to the housing, at least partially in front of the second battery but not the first battery, and (iv) removing the first battery, the knob locking the second battery in the second battery compartment until the first battery is replaced and the knob repositioned.

In an exemplary embodiment, the first battery automatically being partially forced out of the first battery compartment as a result of the knob positioning.

In an exemplary embodiment, the second battery is used to fully operate the intra-aortic balloon pump after the first battery is removed from the housing.

A method, according to an example embodiment of the present invention, minimizes or completely avoids power supply disruption to a device. The device, e.g., a medical device such as an intra-aortic balloon pump or a ventilator, etc., includes a housing defining a first housing part and a second housing part and a lock element connected to the housing. The first housing part is configured to hold a first power source and the second housing part is configured to hold a second power source. The first housing part includes a first opening large enough for the first power source to pass through and the second housing part including a second opening large enough for the second power source to pass through. The method includes the steps of: (a) while the first power source is in the first housing part and the second power source is in the second housing part, moving the lock element from a first position at least partially blocking both the first opening and the second opening to a second position at least partially blocking the first opening and not blocking the second opening, such that the second power source can be removed from the second housing part and the first power source cannot be simultaneously removed from the first housing part; and (b) removing the second power source from the second housing part.

According to an example embodiment, the lock element is positioned between the first and second openings and moveable between (i) a first position, at least partially blocking the first opening but not the second opening, (ii) a second position at least partially blocking the first opening and the second opening, and (iii) a third position at least partially blocking the second opening but not the first opening.

According to an example embodiment, the lock element is a latch-type mechanism including a latch. In the first position, the latch blocks removal of both the first and second power sources. In the second position, the latch blocks removal of only the first power source. In the third position, the latch block removal of only the second power source.

According to an example embodiment, the method further includes the step of replacing the second power source and then moving the lock element back to the first position.

According to an example embodiment, the method further includes the step of restricting motion of the lock element away from the first position until the second power source has been replaced.

Reference throughout this specification to "an embodiment" or "an example embodiment" or "an exemplary embodiment" means that a particular feature, structure, or characteristic described in connection with the embodiment is included in at least one embodiment of the present invention. Thus, the appearances of these phrases in various places throughout this specification are not necessarily all referring to the same embodiment. Furthermore, the particular features, structures, or characteristics may be combined in any suitable manner in one or more embodiments.

An example embodiment of the present invention is described in more detail below with reference to the appended Figures. The foregoing description and examples have been set forth as mere illustrations and are not intended to be limiting. Each of the disclosed aspects and embodiments may be considered individually or in combination with other aspects, embodiments, and variations thereof. The steps of the methods described herein are not confined to any particular order of performance.

BRIEF DESCRIPTION OF THE DRAWINGS

FIGS. 2A-2C illustrate different positions of a lock element. FIG. 2D is the power-source housing of FIG. 2B with one of the power sources ejected.

FIG. 3 is a flowchart of a method according to an example embodiment of the present invention.

FIG. 5 is a front perspective view of an example power-source housing with one of the power sources partially ejected.

DETAILED DESCRIPTION OF THE PRESENT INVENTION

Figure 1:
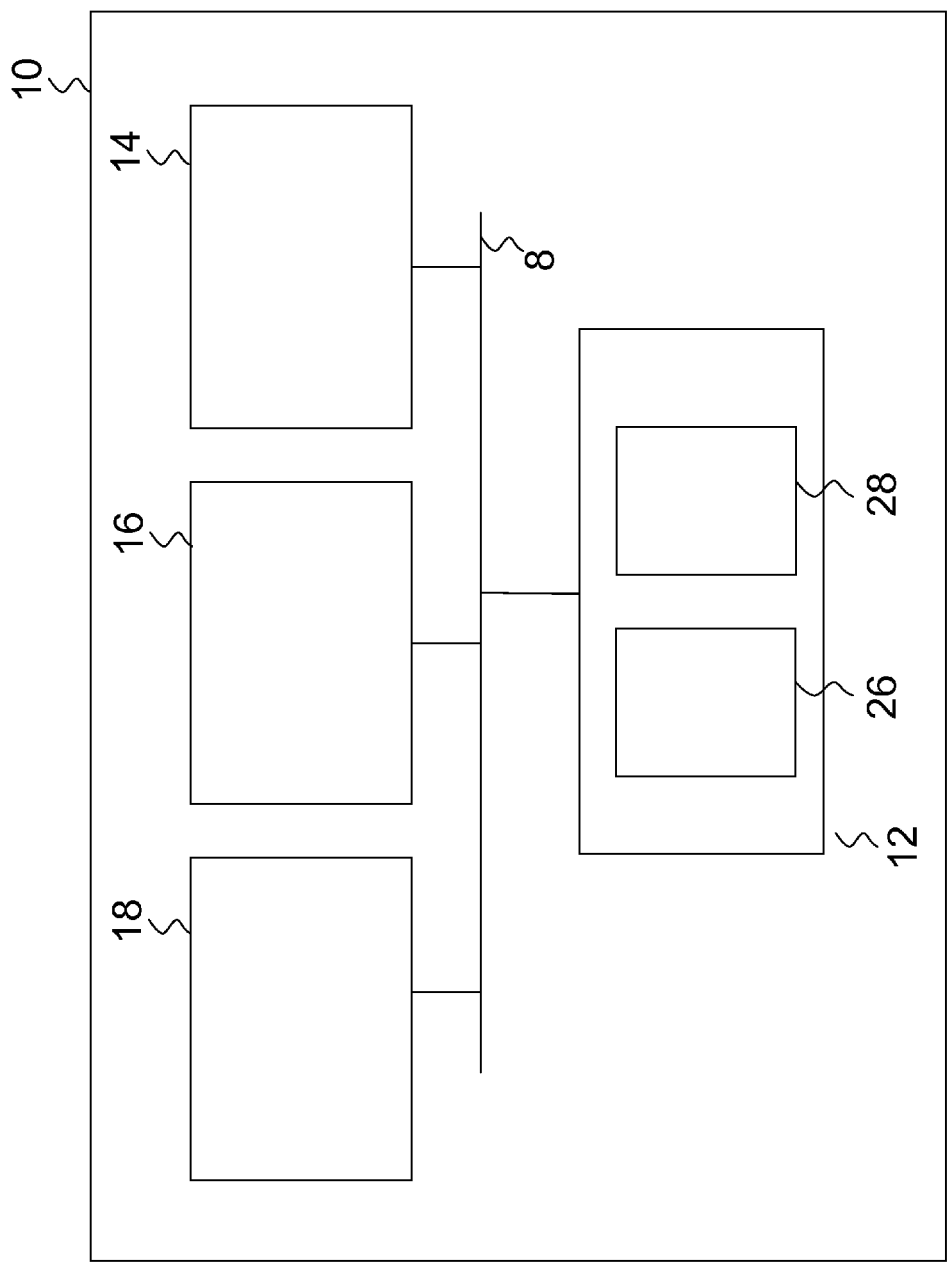
FIG. 1 is a block diagram illustrating components of an intra-aortic balloon pump according to an example embodiment of the present invention.

FIG. 1 illustrates a block diagram of an intra-aortic balloon pump (IABP) 10 according to an exemplary embodiment of the present invention. The IABP 10 is used to inflate and deflate a balloon on a distal end of a balloon catheter (not shown). The balloon catheter is typically inserted into a blood vessel of a patient and used to support the patient's heart. As detailed in U.S. Pat. No. 6,241,706, herein incorporated by reference in its entirety, the IABP 10 includes a power supply 12, a pump 14 (used interchangeably herein with compressor), a control unit 16, and bus 8. The power supply 12 will be discussed in more detail below. The control unit 16 includes a processor/CPU and a computer-readable storage medium for processing and storing data and/or instructions used by any of the other components of the IABP 10. The control unit 16 communicates with the various components of the IABP 10 through bus 8. The IABP 10 also includes a user input interface and display 18. The user input interface and display 18 is preferably a touch-screen monitor, but can be separated into its functional components of a monitor and a keyboard or a mouse.

The power supply 12 of IABP 10 is designed to minimize the likelihood of a power flow disruption to the IABP 10 by limiting the user's ability to remove, e.g., simultaneously, more than one power source at a time. The power supply 12 includes multiple user-removable power sources 26, 28 stored in a power-source housing 22. The user-removable power source may be a rechargeable battery, as shown positioned in a left side of power-source housing 22 in FIGS. 2A-2C. Additionally, the user-removable power source may be an AC and/or DC power-supply module, shown in FIGS. 2A-2D fitting inside a right side of the power-source housing 22. The AC and/or DC power-supply module is attachable to a power cord that can be plugged into a wall or vehicle power outlet. Alternatively, such a power-supply module may be non-removable.

The power-source housing 22 includes a first housing part 45 and a second housing part 47 for holding and connecting to two user-removable power sources 26, 28, although the housing 22 may be expanded to accommodate additional power sources. The power sources 26, 28 connect to electrical connectors 25, 27 located in the back of the power-source housing 22, as depicted in FIG. 2D. Electrical connectors 27 (the second is hidden behind power source 28) removably connects each of the power sources 26, 28 to a power slot interface and includes 4 power pins and 12 signal pins. The signal pins are used to transmit signals and data through bus 8 to the control unit 16 or various sensors.

In various embodiments, the types of power sources include, or are combinations of, a battery (e.g., a 12-volt rechargeable battery), an AC power supply, a DC power supply, a fuel cell, a photovoltaic cell or other equivalents capable of outputting electrical energy. For example, a battery can be used together with an AC power supply.

In an example embodiment, the IABP 10 can fully operate on the power delivered by one of the power sources 26, 28. Further, when the power of one of the power sources 26, 28 is not available in a sufficient capacity, the IABP 10 may automatically draw power from the remaining power source.

Figure 2A:
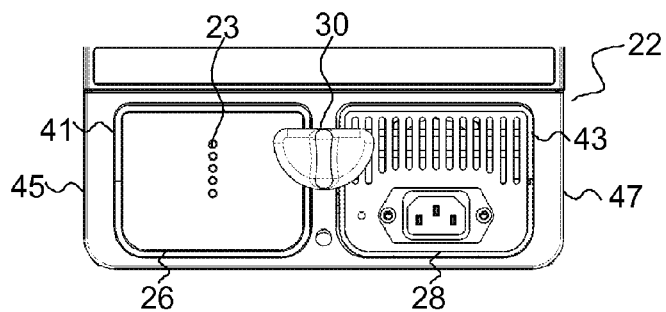
FIGS. 2A-2D are front views of an IABP power-source housing according to an example embodiment.
Figure 2B:
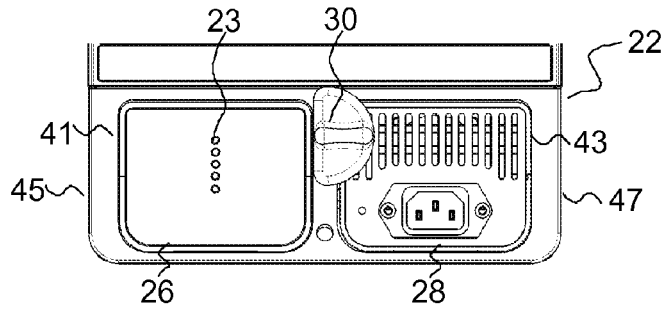
Figure 2C:
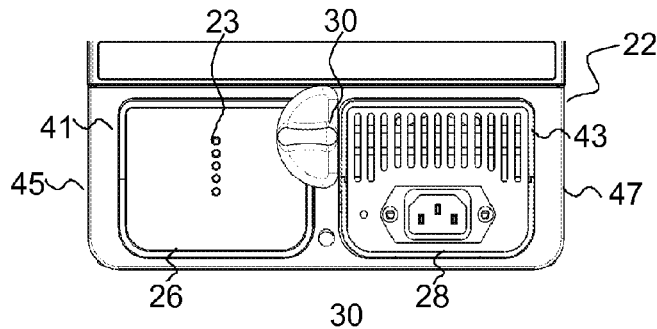
Figure 2D:
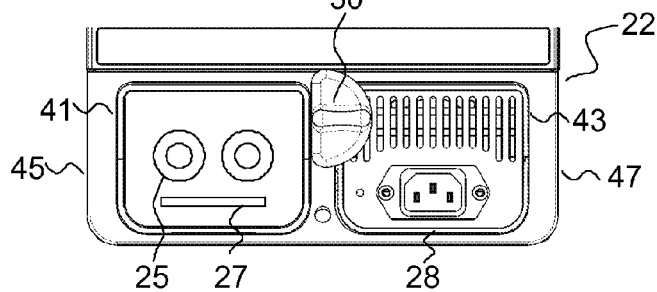

FIGS. 2A-2D illustrate power-source housing 22 configured to hold two power sources. As can be seen in the front views of FIGS. 2A-2C, power-source housing 22 holds battery 26 in the first housing part 45 and AC power-supply module 28 in the second housing part 47. A front opening 41 in the first housing part is large enough for battery 26 to pass through and a front opening 43 in the second housing part is large enough for the AC power-supply module 28 to pass through. The power sources 26, 28 are maintained inside housing 22 via a lock element, knob 30, as shown in FIGS. 2A-2C. Knob 30 is hand operated by the user and its motion may be confined to specific positions, for example, defined by a spring-ball or detent system (shown in FIGS. 4B and 5). FIG. 2D illustrates the power-source housing 22 with power source 26 removed through the front opening 41.

The power-source housing 22 is configured to enable hot-swapping of power sources 26, 28 so as to avoid a loss of power to the IABP 10. In FIG. 2A, both battery 26 and AC power-supply module 28 are maintained within the power-source housing 22 by knob 30. The edges of knob 30 at least partially block the front openings 41, 43 in the power-source housing 22 such that power sources 26, 28 cannot fit through the partially blocked front openings 45, 47. The power-source housing 22 is designed such that rotating the knob 30 ninety degrees in a counterclockwise direction from its position of FIG. 2A to its position in FIG. 2B, clears access to and allows for removal of power source 26 through front opening 41. Rotation of the knob 30 ninety degrees in a clockwise direction from its position of FIG. 2A to its position in FIG. 2C has the same effect with respect to power source 28. This configuration prevents simultaneous removal of the power sources 26, 28.

The knob 30 may be configured to be fixed in a specific position, e.g., in a third position blocking removal of power source 28 as illustrated in FIGS. 2B and 2D, until one or more predetermined conditions are met. One condition may be that power source 26 is reinserted into the first housing part 45. Another condition may be that power source 26 is charged above a predetermined level, e.g., a level higher than the current charge level of power source 28 if a battery, as determined by the control unit 16.

Insertion of power sources 26, 28 is completed as follows. Knob 30 is rotated to a position allowing unobstructed access to one side of the housing 22. One of power sources 26, 28 is then fully inserted into this side of the housing 22. Next, knob 30 is rotated in the opposite direction, e.g., counter clockwise, over the inserted power sources, providing unobstructed access to the opposite side of the housing 22. The second of power sources 26, 28 is then fully inserted into this opposite side of housing 22. Knob 30 is then rotated back, e.g., clockwise, so that it partially covers the entrance for both of the power sources 26, 28. In this state, both power sources 26, 28 are fully inserted and secured in place via knob 30.

In a similar manner, the power sources 26, 28 can be removed based on providing unobstructed access to the appropriate side of the housing 22. FIG. 3 depicts an example embodiment of a method for removing a power source 26, 28. In Step 80, a user moves lock element from a first position at least partially blocking the left side of housing 22 and the right side of housing 22 to a second position at least partially blocking the left side of housing 22 and not blocking the right side of housing 22. Then, in Step 90, the user removes a power source 26, 28 through the right side of housing 22, which has been unobstructed by Step 80.

The lock element may be implemented in different configurations. For example, the lock element can also be a sliding latch, sliding bolt latch or a sliding bolt locking latch such that the lock element can be confined and optionally locked to specific positions similar to those above. Such a lock can (i) slide to the far left such that only power source 28 can be removed, (ii) slide to the far right such that only power source 26 can be removed, or (iii) be centered such that neither of power sources 26, 28 can be removed.

In various embodiments, the IABP 10 can inform the user, e.g., via the user input interface and display 18 or on the battery itself, about which power source can be removed. This benefits the user to ensure that a power source without further power (e.g., an empty battery or an unplugged AC power-supply module) is not the only remaining power source in the system. In one embodiment, the batteries have indicator lights 23 showing how much power is remaining in each battery. In a two-battery system, a user can read the indicators lights to identify which power source is discharged and turn the knob 30 to remove the identified power source. In other embodiments, a sensor or a circuit (not shown) for detecting a power source's characteristics, such as its voltage, can be used to notify the user by displaying a warning or instructions on user input interface and display 18 and/or sounding an audible alarm from the IABP 10, or fix or restrict movement of knob 30 as discussed below.

Figure 4B:
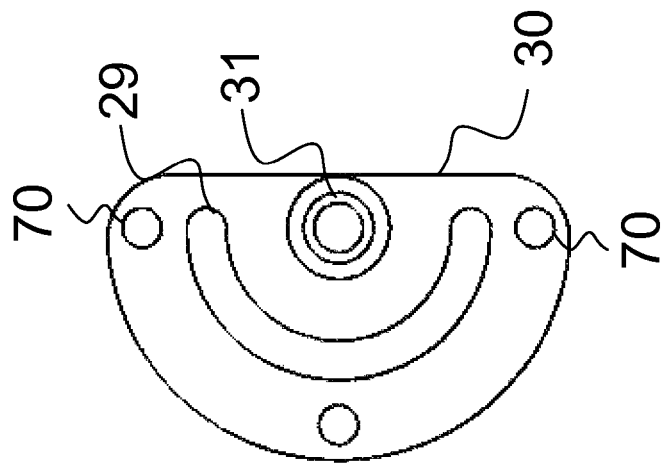
FIG. 4B is a rear view of the lock element of FIGS. 2A-2D.
Figure 4A:
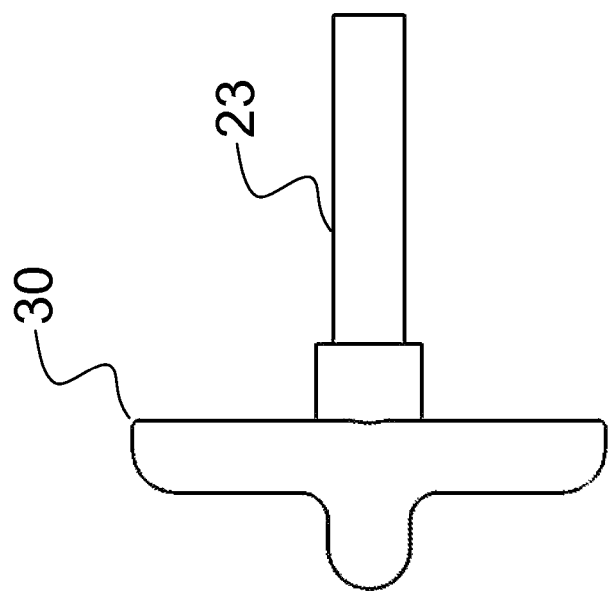
FIG. 4A is a side view of the lock element of FIGS. 2A-2D.

FIGS. 4A and 4B illustrate a side and rear view of knob 30. The knob 30 is connected to or through the front of power-source housing 22 with an integral connector 23 or a retainer 37 (shown in FIG. 6). Knob 30 snaps into place via a detent 31 (shown in FIG. 6) or a spring-ball mechanism (not shown) matching up with recess holes 70. A recess groove 29 in a back surface of the knob may cooperate with a projection 33 (shown in FIG. 6) on the front support 38 (shown in FIG. 6) so as to limit the direction of rotation of the knob 30 between the positions shown in FIGS. 2A-2C. Recess holes 70 can also be used for fixing movement of knob 30 (discussed in more detail later).

Figure 6:
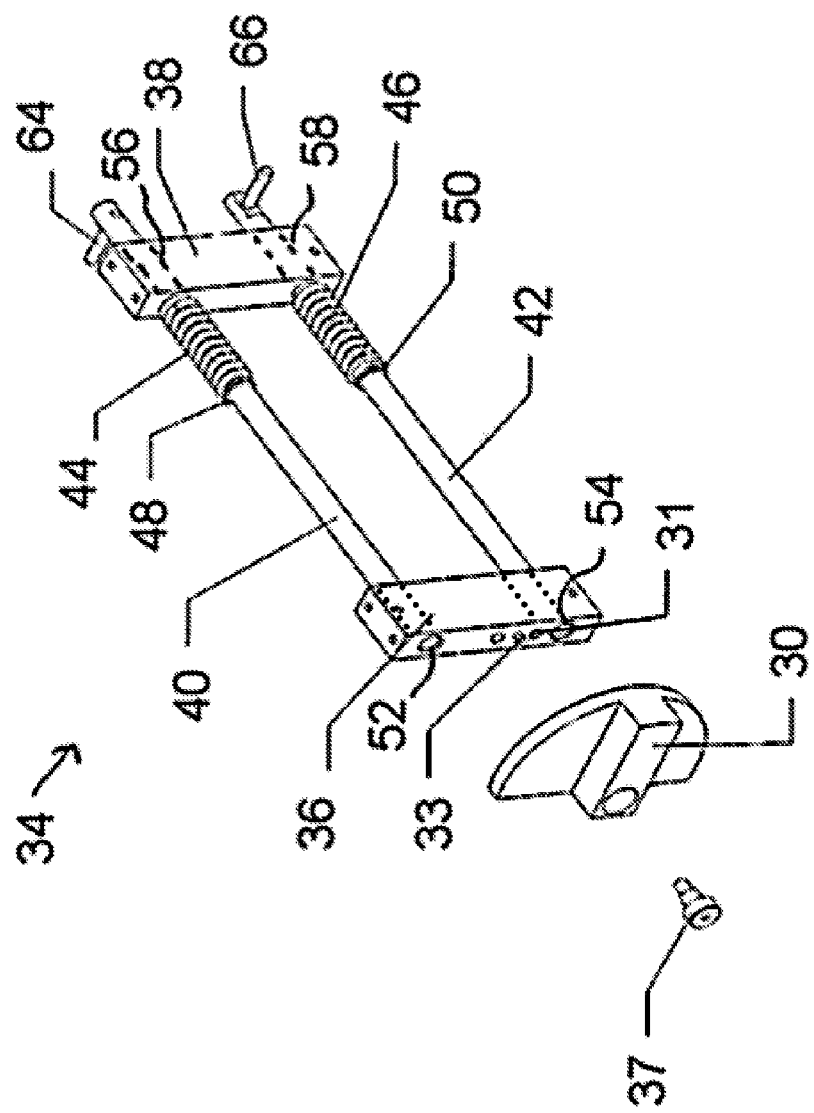
FIG. 6 is a front perspective view of a mechanism from inside the power-source housing of FIG. 5 with the knob removed.

The rear of power-source housing 22 may optionally contain internal spring-based elements, as illustrated in FIG. 2D (spring-based elements 25) and FIG. 6 (spring-based elements 44, 46), to help eject the power sources 26, 28 from the power source housing 22 as soon as they are unlocked or disengaged. In such embodiments, the power-source housing 22 is designed such that rotating the knob 30 ninety degrees to unblock the partially blocked openings results in the unblocked power source 26, 28 being partially forced out in the forward direction of housing 22 by spring-based elements a length L (see FIG. 5) sufficient to allow a user to grasp one of the power source 26, 28 for removal purposes. Length L is preferably less than half of the length of the power source 26, 28, and more preferably, less than a quarter of the length of the power source 26, 28 such that the power source 26, 28 is not completely forced out of housing 22. For example, if a power source is six inches (15.24 cm.) long, then an exemplary length L can be one inch (2.54 cm.). Spring-based elements should have a sufficient spring force to force power sources 26, 28 forward in case 24 a predetermined distance (length L) while allowing a normal user to insert power sources 26, 28 against the spring force.

FIG. 5 shows an exemplary embodiment of a power-source housing 22 having batteries 26, 28 with battery 28 partially forced out in the forward direction a length L due to the exposing of a front surface 32 of battery 28.

Figure 7:
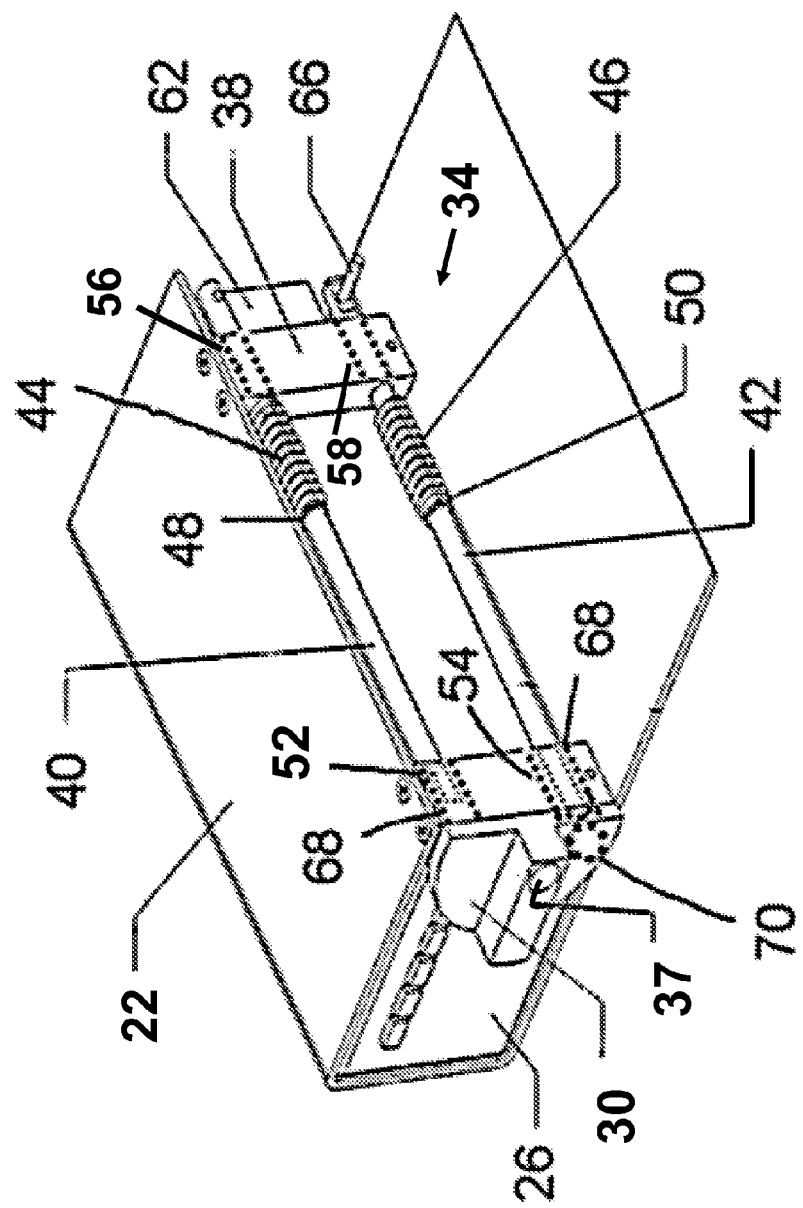
FIG. 7 is a front perspective view of the power-source housing of FIG. 5 with a portion of the case and one of the power-sources not shown.

FIG. 6 is a perspective view of a mechanism 34 used together with the knob 30 and housing 22 to achieve the above ejection and withdrawal safety features. Mechanism 34 is surrounded on both sides by two sidewalls 60, 62 on either side (shown in FIGS. 7-8). FIG. 7 shows the housing 22 with the portion over power source 28 and sidewall 62 removed exposing mechanism 34. The mechanism 34 is positioned in the housing 22 between the power sources 26, 28 and includes front and rear supports 36, 38, rods 40, 42, and spring-based elements 44, 46. Spring-based elements 44, 46 are disposed over and connected to rods 40, 42 via clips 48, 50. Rods 40, 42 pass through bores 52, 54 in the front support 36 and bores 56, 58 in the rear support 38 (all four bores shown as dashed lines in FIGS. 6 and 7). Knob 30 is pivotally secured to front support 36 via a retainer 37.

When knob 30 is rotated such that it extends in front of power source 26 and no longer restrains forward movement of power source 28, as illustrated in FIG. 5, spring-based element 46 forces rod 42 forward. Power source 28 is forced forward by projection 66 on rod 42 a sufficient distance so as to allow a user to grasp the power source 28 for removal. The forward movement of rod 42 shifts a forward end 68 of rod 42 into a recess hole 70 (shown in dashed lines) in a back surface of the knob 30, preventing further rotation of knob 30. Thus, so long as power source 28 is not replaced or inserted to a sufficient depth to engage projection 66, rod 42 locks knob 30 into position in front of power source 26 preventing removal of power source 26. FIG. 7 depicts the housing 22 with power source 28 removed and the portion of the housing 22 surrounding the power source 28 removed except for the base.

The mechanism 34 works the same way when power source 26 is removed preventing removal of power source 28 until power source 26 is replaced. When knob 30 is rotated such that it extends solely in front of power source 28, power source 26 is forced forward by spring-based element 44 (which shifts projection 64 on rod 40) and a forward end 68 of rod 40 shifts into recess 70 and locks knob 30 in place over power source 28.

Figure 8:
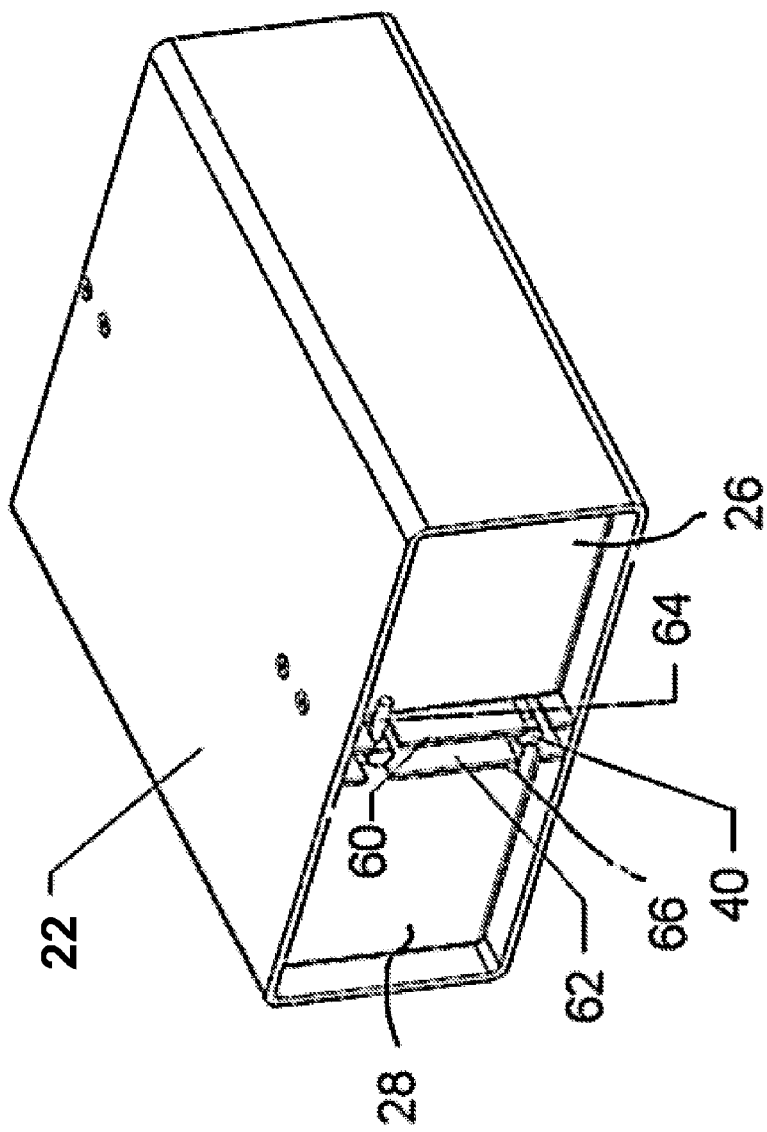
FIG. 8 is a rear perspective view of the power-source housing of FIG. 5.

Once power sources 26, 28 are installed in housing 22, only one of the power sources 26, 28 can be removed from the housing 22 at a time. As power source 26 is positioned in housing 22 it bears against projection 64 and forces rod 40 rearward compressing spring-based element 44. Similarly, as power source 28 is inserted to a sufficient depth in housing 22, it bears against projection 66 forcing rod 42 rearward compressing spring-based element 46. In this exemplary state, illustrated in FIGS. 2A and 5, only detente 31 maintains knob 30 in position in front of both batteries 26, 28. As can be seen in FIG. 8, which shows a rear perspective view of housing 22, projections 64 and 66 lie behind and contact a rear surface of power sources 26, 28.

In an example embodiment, the spring force of spring-based elements 44, 46 should be sufficient to force power sources 26, 28 forward in housing 22 a predetermined distance, e.g., sufficient for a user to grasp one end of the power source for removal purposes. However, additional spring-based elements connected to the back of power sources 26, 28 or placed within housing 22 may also be used. Alternatively, weaker spring-based elements 44, 46 may be used solely for locking purposes. The power sources 26, 28 may be manually removed, for example, by pulling on a ring or handle (not shown) connected to a front surface of the power sources 26, 28, or partially ejected through spring-based elements 25 (as shown in FIG. 2D).

In an example embodiment, the power-source housing 22 is designed so as to assure that at all times one of the power sources 26, 28 remains inside case 24 in a functioning position, i.e., a position in which it can deliver current to the IABP 10 through electrical connector 27 in the power-source housing 22. As depicted in FIG. 5, when power source 28 is released from housing 22, power source 26 is locked in housing 22 by knob 30. Knob 30 may be locked into position over power source 26 until power source 28 is fully replaced or alternatively may be rotatable so as not to lock the knob but just to pose an additional obstacle and prevent simultaneous removal of the power supplies 26, 28. Similarly, when power supply 26 is released, access to power supply 28 is blocked by knob 30. In the embodiment incorporating a lockable knob 30, knob 30 remains over power source 28 and is not rotatable until power source 26 is fully replaced.

In an example embodiment, additional power sources may used to power the IABP 10. For example, two housing elements may be used to house a total of four batteries or other power sources. In this embodiment, two batteries would be installed at all times, and mechanism 34 prevents removal of more than two batteries or power sources at a time from a given housing 22.

The term battery as used herein includes multiple stacked batteries fit within a single battery housing. Power source 26, for example, can include multiple stacked cells placed in first housing part 45. The cells may be stacked vertically or horizontally. Projections 64 and 66 may be increased in length or height to assure that they contact the rear surface of all the stacked cells.

In an example embodiment, compression spring-based elements (not shown), placed behind rods 40 and 42, may be used together with or as an alternative to spring-based elements 44, 46. The rear wall of the housing 22 (not shown in FIG. 7 for clarity) may provide a surface against which the compression spring-based elements could bear.

In an example embodiment, bearings (not shown) or a low friction surface material may be provided on an inside bottom surface of housing 22 to facilitate forward movement and removal of power sources 26, 28.

In an example embodiment, parts of mechanism 34 may be replaced with an electro-mechanical servo and switch system. A first switch inside housing 22 may be used to detect the presence of power source 26 and a second switch inside housing 22 may be used to detect the presence of power source 28. When control unit 16 in communication with the switches determines that only the first switch is triggered, i.e., only power source 28 is present in housing 22, it directs the servo to lock power source 28 in housing 22, for example, by rotating knob 30 such that it lies in front of power source 28 but not power source 26. Similarly, when only the second switch is triggered, the control unit 16 directs the servo to lock power source 26 in housing 22 by rotating the knob 30 in the opposite direction such that it lies in front of power source 26. The servo may also be connected to any other type of locking mechanism. As indicated above, control unit 16 may impose additional conditions which must be met before it allows knob 30 to open.

In an example embodiment, solenoids can be utilized to fix movement of knob 30. Similar to the embodiment illustrated in FIG. 5, solenoids (not shown) can be directly or indirectly connected to rods of which the forward end 68 is extendible into recess 70 of knob 30. The solenoids can be located in the front or the back of the power-source housing 22, and the rod length can be adjusted accordingly. When control unit 16 determines that either side of the power-source housing 22 should be locked based on the status of the power sources, the control unit 16 controls a solenoid to engage the forward end 68 of the appropriate rod with recess 70 in the knob, effectively fixing knob 30 and thus locking the opening of the power-source housing 22. This embodiment can be operated with spring-based elements that put forward pressure on the power source, as illustrated in FIG. 2D or in FIG. 6.

Figure 9:
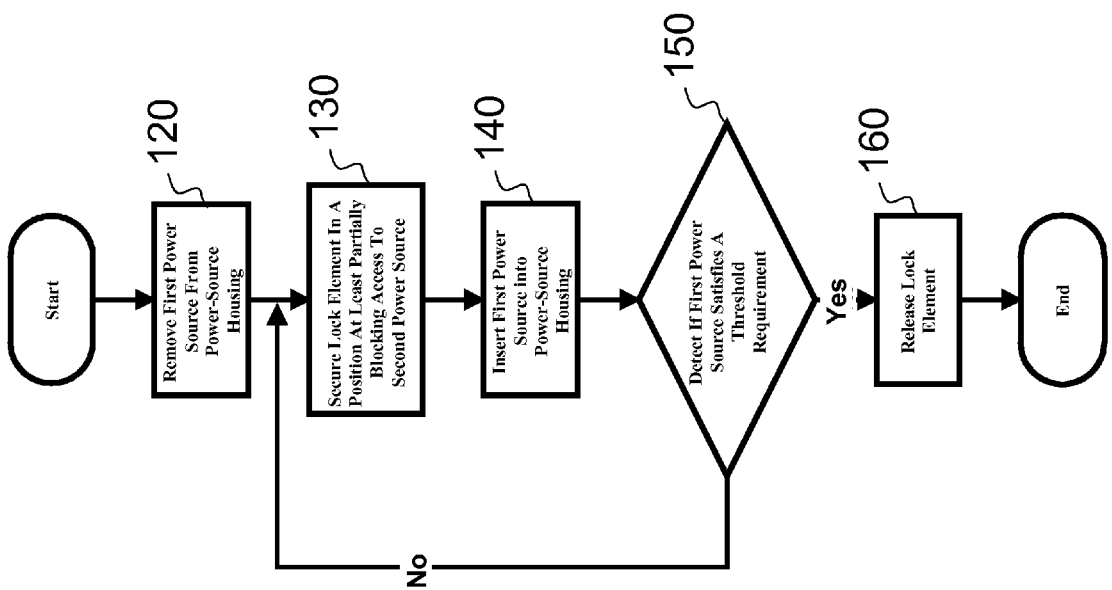
FIG. 9 is a flowchart of a method according to an example embodiment of the present invention.

FIG. 9 illustrates a method according to an example embodiment of the present invention for fixing the lock element or knob 30 over the power source that the IABP 10 determines should not be removed. In Step 120, a user removes a first power source. For removal of the first power source, the locking element is in a position that prevents access to the second power source. In Step 130, the locking element is fixed in the position that prevents access to the second power source. In Step 140, a user introduces a first power source into the power-source housing. In Step 150, the control unit determines whether the first power source satisfies a threshold requirement. A threshold requirement can be determined based on detectable characteristics of the power sources such as any combination of voltage, current, temperature, expected battery life remaining, manufacturer, etc. If the first power source satisfies the threshold requirement, then, in Step 160, the control unit de-fixes or releases the lock element so that user can move the lock element. If not, the control unit maintains the lock secured.

Figure 10:
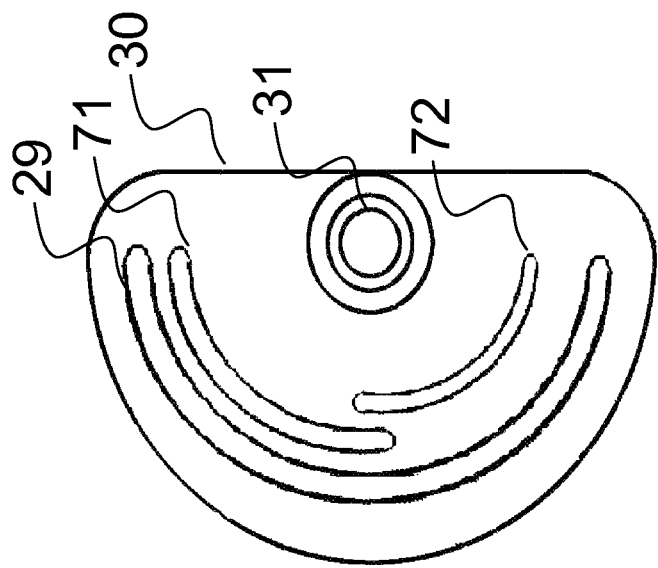
FIG. 10 is a rear view of a lock element according to an example embodiment of the present invention.

In addition to or in place of hole recesses 70 used in the embodiment shown in FIG. 4B, knob 30 can include grooves to restrict the direction of rotation. FIG. 10 illustrates an exemplary knob containing partial grooves 71, 72. These recess partial grooves 71, 72 are used in connection with a solenoid-controlled rod that enters the grooves based on the IABP's detection of the power source states or operating characteristics. Partial recess groove 71 restricts rotation of knob 30 from the position in FIG. 2A blocking both power sources 26, 28 to the position of FIG. 2B allowing access to one of power sources 26, 28. In a similar manner, partial recess groove 71 restricts rotation from the position in FIG. 2A blocking both power sources 26, 28 to the position of FIG. 2C allowing access to one of power sources 26, 28. Recess groove 29 is preferably included, but optional, to facilitate smooth rotation. FIG. 10 also illustrates recess groove 29 and partial recess grooves 71, 72 as having different widths. Likewise, these grooves may be adapted to have similar and/or different depths and widths to each other depending on the system they are used in. As shown in FIG. 4B and described above, recess holes 70 (not shown in FIG. 10) can optionally be used for locking or snapping into a position.

Sensing of the existence and characteristics of particular power sources can be checked in multiple ways. Switches can detect and limit the amount of power going through them. A system bus controller (not shown) may be used to detect and store which power sources are present, the amount of current drawn from the power sources, the amount of voltage in the power sources, the temperature of the power sources, etc. In addition, the system bus controller may detect information that can be stored in the power sources themselves. For example, the power sources may have memory in the form of circuitry or software that contains (i) error codes about states of the power source, (ii) the amount of remaining expected life in a battery or (iii) a temperature inside a power supply.

Figure 11:
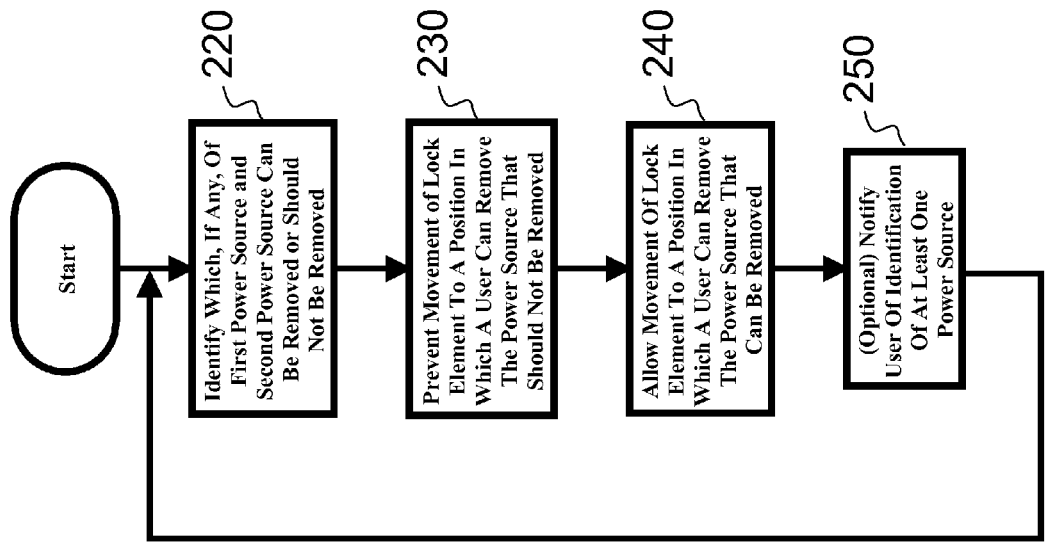
FIG. 11 is a flowchart of a method according to an example embodiment of the present invention.

FIG. 11 illustrates an example method that prevents movement of a locking element, such as knob 30, to a position that allows access to a power source that the IABP 10 determines should not be removed. In Step 220, the control unit identifies based on a detection of power source characteristics whether a power source that is present should not be removed and whether a power source is present that can be removed. In Step 230, the control unit prevents movement of the lock element to a position that allows access to the power source identified that should not be removed. In Step 240, the control unit allows movement of the lock element to a position that allows access to the power source identified as can be removed. The control unit can optionally notify the user of this identification through status lights 23 on the power source, status lights on the power source compartment, IABP 10 or locking element (not shown) or through the user input interface and display 18.

Although IABP 10 is described above, the exemplary embodiments described above can be used in other similar systems where maintaining power is important, especially medical devices and systems used in a hospital, such as a heart-lung machine.

Those skilled in the art can appreciate from the foregoing description that the present invention can be implemented in a variety of forms. Therefore, while the embodiments of this invention have been described in connection with particular examples thereof, the true scope of the embodiments of the invention should not be so limited since other modifications and variations will become apparent to the skilled practitioner upon a study of the drawings and specification. Such modifications and variations are considered to be within the purview and scope of the appended claims and their equivalents.

What is claimed is:

1. An intra-aortic balloon pump, comprising:
a pump;
a lock element comprising a rotatable knob;
a power-source housing; and
a control unit adapted to control the pump,
wherein an interior of the power-source housing comprises a first housing part and a second housing part, the first housing part configured to hold a first power source that is operably connectable to the control unit, the second housing part configured to hold a second power source that is operably connectable to the control unit, the first housing part including a first opening large enough for the first power source to pass through, the second housing part including a second opening large enough for the second power source to pass through, the power-source housing accessible such that the first power source and the second power source can be replaced without dismantling the intra-aortic balloon pump, and the power-source housing configured such that when the first power source is being removed from the first housing part the rotatable knob prevents simultaneous removal of the second power source from the second housing part and when the second power source is being removed from the second housing part the rotatable knob prevents simultaneous removal of the first power source from the first housing part.

2. The intra-aortic balloon pump according to claim 1, wherein the first power source is capable of being replaced while the second power source is powering the intra-aortic balloon pump and the second power source is capable of being replaced while the first power source is powering the intra-aortic balloon pump.

3. The intra-aortic balloon pump according to claim 1, wherein one of (a) the first and second power sources are both batteries, (b) the first power source is a battery and the second power source is an AC or DC power supply, and (c) the first and second power sources are both AC or DC power supplies.

4. The intra-aortic balloon pump according to claim 1, wherein the rotatable knob is positioned between the first and second openings, and the rotatable knob is movable between a first position at least partially blocking the first opening but not the second opening, a second position at least partially blocking the first opening and the second opening, and a third position at least partially blocking the second opening but not the first opening.

5. The intra-aortic balloon pump according to claim 4, wherein the lock element further comprises a solenoid configured to move a rod forward such that a forward end of the rod passes into a recess in the rotatable knob to fix movement of the lock element.

6. The intra-aortic balloon pump according to claim 1, wherein the power-source housing is configured to facilitate removal of the first power source, when the first housing part is transitioned from a locked state to an unlocked state, via the lock element, the first power source is shifted forward in the power-source housing a predetermined distance by one or more mechanisms in the power-source housing.

7. The intra-aortic balloon pump according to claim 6, wherein the one or more mechanisms in the power-source housing is spring-based.

8. The intra-aortic balloon pump according to claim 6, wherein the power-source housing is configured to facilitate removal of the second power source, when the second housing part is transitioned from a locked state to an unlocked state, via the lock element, the second power source is shifted forward in the power-source housing a predetermined distance by the one or more mechanisms in the power-source housing.

9. The intra-aortic balloon pump according to claim 6, wherein the lock element further comprises a mechanism that includes a first rod, the first rod configured such that placing the first power source in the first housing part to a sufficient depth within the power-source housing shifts the first rod rearward away from the first opening against the force of a first spring-based element, subsequent removal of the first battery causing the first rod to move forward such that a forward end of the first rod passes into a recess in the lock element while in the third position.

10. The intra-aortic balloon pump according to claim 9, wherein the mechanism further includes a second rod, the second rod configured such that placing the second power source in the second housing part to a sufficient depth within the housing shifts the second rod rearward away from the second opening against the force of a second spring-based element, subsequent removal of the second battery causing the second rod to move forward such that a forward end of the second rod passes into a recess in the lock element while in the first position.

11. The intra-aortic balloon pump according to claim 6, the lock element further comprises a mechanism that includes a first solenoid and a second solenoid, wherein the lock element contains a first partial recess groove configured to engage a first rod controlled by the first solenoid, and a second partial recess groove configured to engage a second rod controlled by the second solenoid, the first partial recess groove when engaged by the first rod both allows motion between the first position and the second position and restricts motion from the second position to the third position, and the second partial groove when engaged by the second rod both allows motions between the second position and the third position and restricts motion from the second position to the first position.

12. The intra-aortic balloon pump according to claim 1, wherein the power source housing is configured to at least partially eject the first and second power sources from the power source housing through the assistance of a spring structure.

13. An intra-aortic balloon pump, comprising:
a pump;
a control unit adapted to control the pump;
a lock element;
a power source housing for housing a first power source in a first housing part and a second power source in a second housing part, each of the first and second power sources are capable of communicating with the control unit and are removable from the power source housing without dismantling the intra-aortic balloon pump; and
at least one of the first and second power sources is an AC power-supply module that is connectable to a wall or vehicle power outlet while housed within the power source housing or a DC power-supply module that is connectable to a wall or vehicle power outlet while housed within the power source housing, and the other of the first and second power sources is a battery;
wherein the power-source housing is configured such that when the first power source is being removed from the first housing part the lock element prevents simultaneous removal of the second power source from the second housing part and when the second power source is being removed from the second housing part the lock element prevents simultaneous removal of the first power source from the first housing part.

14. The intra-aortic balloon pump according to claim 13, wherein the first and second housing parts each comprise an opening, and wherein the lock element comprises a mechanism positioned between the opening of the first housing part and the opening of the second housing part such that the mechanism is movable between a first position at least partially blocking the first opening but not the second opening, a second position at least partially blocking the first opening and the second opening, and a third position at least partially blocking the second opening but not the first opening.

15. The intra-aortic balloon pump according to claim 13, wherein the lock element comprises a moveable knob and the power-source housing is configured so that when the first power source is removed from the first housing part the knob has moved to a position that blocks simultaneous removal of the second power source from the second housing part and when the second power source is removed from the second housing part the knob has moved to a position that blocks simultaneous removal of the first power source from the first housing part.

16. An intra-aortic balloon pump, comprising:
a pump;
a lock element;
a power-source housing that houses a power supply; and
a control unit adapted to control the pump and operably connected to the power supply, wherein the power-source housing comprises a first housing part and a second housing part, wherein the first housing part is configured to hold a first power source of the power supply and the second housing part is configured to hold a second power source of the power supply, wherein the first housing part includes a first opening large enough for the first power source to pass through and the second housing part includes a second opening large enough for the second power source to pass through, wherein the power-source housing is accessible so that the first power source and the second power source are replaceable without dismantling the intra-aortic balloon pump, and the power-source housing is configured so that when the first power source is removed from the first housing part the lock element prevents simultaneous removal of the second power source from the second housing part, and when the second power source is removed from the second housing part the lock element prevents simultaneous removal of the first power source from the first housing part, wherein the power source housing is configured to at least partially eject the first power source and the second power source from the power source housing through the assistance of a spring structure.

17. A method of minimizing power supply disruption to a device, wherein the device is an intra-aortic balloon pump according to claim 16, and the method comprises the steps of:
while the first power source is in the first housing part and the second power source is in the second housing part, moving the lock element from a first position at least partially blocking both the first opening and the second opening to a second position at least partially blocking the first opening and not blocking the second opening, such that the second power source can be removed from the second housing part and the first power source cannot be simultaneously removed from the first housing part; and removing the second power source from the second housing part.

18. The method of claim 17, wherein the device is an intra aortic balloon pump.

19. The method of claim 17, wherein the lock element is a latch-type mechanism including a latch, in the first position the latch blocks removal of both the first and second power sources, in the second position the latch blocks removal of only the first power source, and in the third position the latch block removal of only the second power source.

20. The method of claim 17, further comprising the step of replacing the second power source and then moving the lock element back to the first position.

21. The method of claim 17, further comprising the step of restricting motion of the lock element away from the first position until the second power source has been replaced.

22. An intra-aortic balloon pump, comprising:
a pump;
a control unit adapted to control the pump;
a lock element;
a power source housing that houses a first power source in a first housing part and that houses a second power source in a second housing part, wherein each of the first power source and the second power source is connectable to communicate with the control unit and is removable from the power source housing without dismantling the intra-aortic balloon pump,
wherein at least one of the first power source and the second power source is an AC power-supply module or a DC power-supply module that is connectable to a wall or vehicle power outlet while housed within the power source housing, wherein the power-source housing is configured so that when the first power source is removed from the first housing part the lock element prevents simultaneous removal of the second power source from the second housing part and when the second power source is removed from the second housing part the lock element prevents simultaneous removal of the first power source from the first housing part, and
wherein the first housing part comprises a first opening and the second housing part comprises a second opening, and wherein the lock element comprises a mechanism positioned between the first opening of the first housing part and the second opening of the second housing part so that the mechanism is movable between a first position at least partially blocking the first opening but not the second opening, a second position at least partially blocking the first opening and the second opening, and a third position at least partially blocking the second opening but not the first opening.

23. An intra-aortic balloon pump, comprising:
a pump;
a lock element comprising a solenoid configured to move a rod forward so that a forward end of the rod passes into a recess in the lock element to fix movement of the lock element;
a power-source housing that houses a power supply; and
a control unit adapted to control the pump and operably connected to the power supply, wherein the power-source housing comprises a first housing part and a second housing part, wherein the first housing part is configured to hold a first power source of the power supply and the second housing part is configured to hold a second power source of the power supply, wherein the first housing part includes a first opening large enough for the first power source to pass through and the second housing part includes a second opening large enough for the second power source to pass through, wherein the power-source housing is accessible so that the first power source and the second power source are replaceable without dismantling the intra-aortic balloon pump, and the power-source housing is configured so that when the first power source is removed from the first housing part the lock element prevents simultaneous removal of the second power source from the second housing part, and when the second power source is removed from the second housing part the lock element prevents simultaneous removal of the first power source from the first housing part.

* * * * *